US010213237B2

(12) United States Patent
Wiederkehr

(10) Patent No.: US 10,213,237 B2
(45) Date of Patent: Feb. 26, 2019

(54) PERIPROSTHETIC EXTENSION PLATE

(71) Applicant: Stryker European Holdings I, LLC, Kalamazoo, MI (US)

(72) Inventor: Andreas Wiederkehr, Biel/Bienne (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 1140 days.

(21) Appl. No.: 14/506,078

(22) Filed: Oct. 3, 2014

(65) Prior Publication Data
US 2016/0095636 A1 Apr. 7, 2016

(51) Int. Cl.
*A61B 17/80* (2006.01)

(52) U.S. Cl.
CPC ...... *A61B 17/8033* (2013.01); *A61B 17/8014* (2013.01)

(58) Field of Classification Search
CPC ...................... A61B 17/80–17/8095
USPC .................. 606/70, 71, 280–299
See application file for complete search history.

(56) References Cited

U.S. PATENT DOCUMENTS

| 4,388,921 A | 6/1983 | Sutter et al. |
| 4,973,332 A | 11/1990 | Kummer |
| 5,015,248 A | 5/1991 | Burstein et al. |
| 5,053,036 A | 10/1991 | Perren et al. |
| 5,066,296 A | 11/1991 | Chapman et al. |
| 5,151,103 A | 9/1992 | Tepic et al. |
| 5,486,176 A | 1/1996 | Hildebrand et al. |
| 5,531,554 A | 7/1996 | Jeanson et al. |
| 5,531,745 A | 7/1996 | Ray |
| 5,681,313 A | 10/1997 | Diez |
| 5,951,558 A | 9/1999 | Fiz |
| 5,954,722 A | 9/1999 | Bono |

(Continued)

FOREIGN PATENT DOCUMENTS

| DE | 10039767 A1 | 7/2001 |
| FR | 2674118 A1 | 9/1992 |

(Continued)

OTHER PUBLICATIONS

Extended European Search Report for Application No. 15002833 dated Mar. 4, 2016.

(Continued)

*Primary Examiner* — Matthew Lawson
(74) *Attorney, Agent, or Firm* — Lerner, David, Littenberg, Krumholz & Mentlik, LLP

(57) ABSTRACT

A fixation system includes an elongate plate and an extension plate. The elongate plate includes an inner wall and has a longitudinal axis. The extension plate has first and second attachment portions offset from one another. An engagement portion extends outwardly from the first attachment portion. The engagement portion is couplable to the inner wall of the elongate plate. The second attachment portion defines an aperture for receiving a fastener. The second attachment portion is revolvable about the longitudinal axis of the inner wall when the engagement portion is coupled to and movable about the inner wall. A fastener is received into the first attachment portion to attach the extension plate to the elongate plate. Another fastener is received into the second attachment portion and into a bone part.

28 Claims, 4 Drawing Sheets

FIG. 2

(56) References Cited

U.S. PATENT DOCUMENTS

| | | |
|---|---|---|
| 5,976,141 A | 11/1999 | Haag et al. |
| 6,017,345 A | 1/2000 | Richelsoph |
| 6,129,728 A | 10/2000 | Schumacher et al. |
| 6,193,721 B1 | 2/2001 | Michelson |
| D440,311 S | 4/2001 | Michelson |
| 6,221,073 B1 | 4/2001 | Weiss et al. |
| 6,235,003 B1 | 5/2001 | Dysarz |
| 6,235,033 B1 | 5/2001 | Brace et al. |
| 6,258,089 B1 | 7/2001 | Campbell et al. |
| 6,273,889 B1 | 8/2001 | Richelsoph |
| D449,692 S | 10/2001 | Michelson |
| 6,331,179 B1 | 12/2001 | Freid et al. |
| 6,398,783 B1 | 6/2002 | Michelson |
| 6,416,528 B1 | 7/2002 | Michelson |
| 6,428,542 B1 | 8/2002 | Michelson |
| 6,454,769 B2 | 9/2002 | Wagner et al. |
| 6,454,771 B1 | 9/2002 | Michelson |
| 6,503,250 B2 | 1/2003 | Paul |
| 6,520,965 B2 | 2/2003 | Chervitz et al. |
| 6,527,776 B1 | 3/2003 | Michelson |
| 6,533,786 B1 | 3/2003 | Needham et al. |
| 6,533,789 B1 | 3/2003 | Hall, IV et al. |
| 6,572,622 B1 | 6/2003 | Schafer et al. |
| 6,575,975 B2 | 6/2003 | Brace et al. |
| 6,592,586 B1 | 7/2003 | Michelson |
| 6,602,256 B1 | 8/2003 | Hayes |
| 6,616,666 B1 | 9/2003 | Michelson |
| 6,620,163 B1 | 9/2003 | Michelson |
| 6,626,907 B2 | 9/2003 | Campbell et al. |
| 6,645,209 B2 | 11/2003 | Hall, IV et al. |
| 6,652,525 B1 | 11/2003 | Assaker et al. |
| 6,652,530 B2 | 11/2003 | Ip et al. |
| 6,663,632 B1 | 12/2003 | Frigg |
| 6,669,700 B1 | 12/2003 | Farris et al. |
| 6,679,883 B2 | 1/2004 | Hawkes et al. |
| 6,695,846 B2 | 2/2004 | Richelsoph et al. |
| 6,712,818 B1 | 3/2004 | Michelson |
| 6,730,091 B1 | 5/2004 | Pfefferle et al. |
| 6,755,831 B2 | 6/2004 | Putnam et al. |
| 6,890,334 B2 | 5/2005 | Brace et al. |
| 6,890,335 B2 | 5/2005 | Grabowski et al. |
| 6,916,320 B2 | 7/2005 | Michelson |
| 6,926,718 B1 | 8/2005 | Michelson |
| 6,929,646 B2 | 8/2005 | Gambale |
| 6,936,050 B2 | 8/2005 | Michelson |
| 6,936,051 B2 | 8/2005 | Michelson |
| 6,969,390 B2 | 11/2005 | Michelson |
| 6,984,234 B2 | 1/2006 | Bray |
| 7,001,388 B2 | 2/2006 | Orbay et al. |
| 7,074,221 B2 | 7/2006 | Michelson |
| 7,090,676 B2 | 8/2006 | Huebner et al. |
| 7,137,984 B2 | 11/2006 | Michelson |
| 7,175,623 B2 | 2/2007 | Thramann et al. |
| 7,195,633 B2 | 3/2007 | Medoff et al. |
| 7,229,443 B2 | 6/2007 | Eberlein et al. |
| 7,273,481 B2 | 9/2007 | Lombardo et al. |
| 7,303,564 B2 | 12/2007 | Freid et al. |
| 7,326,212 B2 | 2/2008 | Huebner |
| 7,625,381 B2 | 12/2009 | Michelson |
| 7,682,379 B2 | 3/2010 | Mathieu et al. |
| 7,704,251 B2 | 4/2010 | Huebner et al. |
| 7,704,255 B2 | 4/2010 | Michelson |
| 7,758,620 B2 | 7/2010 | Porcher |
| 7,771,458 B2 | 8/2010 | Biedermann et al. |
| 7,780,710 B2 | 8/2010 | Orbay et al. |
| 7,794,482 B2 | 9/2010 | Mathieu et al. |
| 7,833,254 B2 | 11/2010 | Celli et al. |
| 7,887,569 B2 | 2/2011 | Frigg |
| 7,942,913 B2 | 5/2011 | Ziolo et al. |
| 7,972,366 B2 | 7/2011 | Richelsoph et al. |
| 8,075,602 B2 | 12/2011 | Lombardo et al. |
| 8,147,530 B2 | 4/2012 | Strnad et al. |
| 8,172,885 B2 | 5/2012 | Songer et al. |
| 8,177,819 B2 | 5/2012 | Huebner et al. |
| 8,216,283 B2 | 7/2012 | Mathieu et al. |
| 8,221,421 B2 | 7/2012 | Hearn |
| 8,226,692 B2 | 7/2012 | Mathieu et al. |
| 8,287,575 B2 | 10/2012 | Murner et al. |
| 8,337,534 B2 | 12/2012 | Celli et al. |
| 8,388,665 B2 | 3/2013 | Eberlein et al. |
| 8,398,636 B2 | 3/2013 | Simon et al. |
| 8,439,957 B2 | 5/2013 | Lombardo et al. |
| 8,444,680 B2 | 5/2013 | Dooney, Jr. et al. |
| 8,486,116 B2 | 7/2013 | Heilman |
| 8,486,118 B2 | 7/2013 | Mathieu et al. |
| 8,500,737 B2 | 8/2013 | Richelsoph et al. |
| 8,518,042 B2 | 8/2013 | Winslow et al. |
| 8,579,898 B2 | 11/2013 | Prandi et al. |
| 8,652,179 B2 | 2/2014 | Graham et al. |
| 8,668,723 B2 | 3/2014 | Altarac et al. |
| 8,728,129 B2 | 5/2014 | Fritzinger et al. |
| 8,734,494 B2 | 5/2014 | Simon et al. |
| 8,784,458 B1* | 7/2014 | White .................... A61B 17/80 606/288 |
| 8,828,064 B2 | 9/2014 | Ziolo et al. |
| 8,906,070 B2 | 12/2014 | Medoff |
| 8,961,573 B2 | 2/2015 | Gonzalez-Hernandez |
| 8,998,904 B2 | 4/2015 | Zeetser et al. |
| 9,072,557 B2 | 7/2015 | Fierlbeck et al. |
| 9,084,636 B2 | 7/2015 | Mekhail et al. |
| D735,861 S | 8/2015 | Embleton et al. |
| 9,131,968 B2 | 9/2015 | Cavallazzi et al. |
| 9,138,244 B2 | 9/2015 | Mebarak et al. |
| 9,138,267 B2 | 9/2015 | Cavallazzi |
| 9,155,577 B2 | 10/2015 | Pfefferle et al. |
| 9,241,749 B2 | 1/2016 | Lombardo et al. |
| 9,254,154 B2 | 2/2016 | Gonzalez-Hernandez |
| 9,308,033 B2 | 4/2016 | Huebner et al. |
| 9,333,014 B2 | 5/2016 | Gonzalez-Hernandez |
| 9,522,066 B2 | 12/2016 | Segina et al. |
| 2002/0058939 A1 | 5/2002 | Wagner et al. |
| 2003/0187440 A1 | 10/2003 | Richelsoph et al. |
| 2004/0030339 A1 | 2/2004 | Wack et al. |
| 2004/0097935 A1 | 5/2004 | Richelsoph et al. |
| 2004/0102776 A1 | 5/2004 | Huebner |
| 2004/0127896 A1 | 7/2004 | Lombardo et al. |
| 2005/0015131 A1 | 1/2005 | Fourcault et al. |
| 2005/0027296 A1 | 2/2005 | Thramann et al. |
| 2005/0043736 A1 | 2/2005 | Mathieu et al. |
| 2005/0049594 A1 | 3/2005 | Wack et al. |
| 2005/0049595 A1 | 3/2005 | Suh et al. |
| 2005/0187552 A1 | 8/2005 | Michelson |
| 2005/0240187 A1* | 10/2005 | Huebner ................ A61B 17/80 606/71 |
| 2007/0043366 A1 | 2/2007 | Pfefferle et al. |
| 2008/0103501 A1 | 5/2008 | Ralph et al. |
| 2008/0306550 A1 | 12/2008 | Matityahu |
| 2009/0076554 A1 | 3/2009 | Huebner et al. |
| 2009/0192549 A1 | 7/2009 | Sanders et al. |
| 2009/0248087 A1 | 10/2009 | Lewis et al. |
| 2009/0275987 A1 | 11/2009 | Graham et al. |
| 2010/0179552 A1* | 7/2010 | Wolter .................... A61B 17/80 606/71 |
| 2010/0262194 A1 | 10/2010 | Wagner et al. |
| 2011/0112584 A1 | 5/2011 | Frigg |
| 2012/0226321 A1 | 9/2012 | Gonzalez-Hernandez |
| 2013/0041375 A1 | 2/2013 | Fierlbeck et al. |
| 2013/0060251 A1 | 3/2013 | Eglseder, Jr. |
| 2013/0204300 A1 | 8/2013 | Michelson |
| 2013/0211461 A1 | 8/2013 | Christen |
| 2013/0274813 A1 | 10/2013 | Mathieu et al. |
| 2013/0304132 A1 | 11/2013 | Heilman |
| 2013/0345760 A1 | 12/2013 | Lombardo et al. |
| 2014/0148861 A1 | 5/2014 | Simon et al. |
| 2014/0222084 A1 | 8/2014 | Fritzinger et al. |
| 2014/0228895 A1 | 8/2014 | Ziolo et al. |
| 2014/0243907 A1 | 8/2014 | Cavallazzi et al. |
| 2014/0367268 A1 | 12/2014 | Naito et al. |
| 2015/0305877 A1 | 10/2015 | Gargac et al. |
| 2016/0038199 A1* | 2/2016 | Wiederkehr .......... A61B 17/842 606/74 |
| 2016/0310181 A1 | 10/2016 | Frigg |

(56) References Cited

U.S. PATENT DOCUMENTS

FOREIGN PATENT DOCUMENTS

| | | | |
|---|---|---|---|
| FR | 2739151 | A1 | 3/1997 |
| FR | 2744011 | A1 | 8/1997 |
| FR | 2790198 | A1 | 9/2000 |
| FR | 2792185 | A1 | 10/2000 |
| FR | 2 844 702 | A1 | 3/2004 |
| SU | 1130332 | A1 | 12/1984 |
| SU | 1223901 | A1 | 4/1986 |
| SU | 1634260 | A1 | 3/1991 |
| WO | 8201645 | A1 | 5/1982 |
| WO | 9407040 | A1 | 3/1994 |
| WO | 99/09903 | A1 | 3/1999 |

OTHER PUBLICATIONS

Extended European Search Report for Application No. 17000134, dated Aug. 21, 2017.

* cited by examiner

PERIPROSTHETIC EXTENSION PLATE

FIELD OF THE TECHNOLOGY

The present invention relates generally to attachment devices for bone plates, and in particular relates to such devices for treating periprosthetic fractures via the insertion of fixation screws therethrough and into bone.

BACKGROUND OF THE TECHNOLOGY

Bone plates for osteosynthesis or arthrodesis are often fixed to bone substantially parallel to a longitudinal bone axis using screws or other fixation elements. Such bone plates are firmly fixed to the bone to prevent bone parts or fragments from moving relative to each other. When fixing a bone plate to bone particular care is to be taken in cases of peri-implant fractures, including periprosthetic fractures, for example. Periprosthetic fractures are fractures around a joint or other prosthesis, whereas peri-implant fractures more generally denote fractures around any type of implant.

When a periprosthetic fracture is to be treated, in which a prosthetic device (e.g., with a ball joint and a stem) partially extends into a medullary canal of the fractured bone, the surgeon generally has to keep in mind that the fixation elements repairing the fracture must not intrude into the medullary canal where the prosthetic device has been inserted. In such cases, an attachment device can be used which is adapted to accommodate the bone plate.

Each of U.S. Pat. No. 4,973,332 and U.S. Patent Application Publication No. 2010/0262194 discloses periprosthetic repair systems comprising a long bone plate and an attachment device. The long bone plates shown are configured to hold fracture parts of the long bone together to promote healing of the fractured bone, for example. The attachment devices are adapted to be arranged on the long bone plates. Specifically, the attachment devices form a partial overlay which fits over and accommodates the long bone plate.

These attachment devices also include finger-like structures or wings that are inclined with respect to a central portion of the attachment devices and are adapted to extend around at least a portion of the femur. For anchoring the attachment devices in the femur, each wing has a hole for receiving a screw which is screwed into the femur.

When attaching the long bone plate using the attachment device, it is desired that this attachment offers a high stability so that the bone fragments of the fractured long bone can effectively consolidate. However, when a prosthetic device extends along the length of the bone, the screws for anchoring the attachment device are preferably anchored in the outer hard layer of the bone. That is, they preferably should not penetrate into the medullary canal of the bone.

The attachment device of the repair system disclosed in U.S. Patent Application Publication No. 2010/0262194 further includes receiving holes that are aligned to receive fixation elements that do not pass through a longitudinal axis of the medullary canal. However, aligning the receiving holes requires fixing the attachment device to the long bone plate with a fixation element or, in the alternative, clumsily sliding the attachment device over the plate prior to fixation of the attachment device to the plate to an appropriate position of the receiving holes and in which the long bone plate and the attachment device are aligned for attachment to each other.

Thus, there exists a need for a way in which to align an attachment portion for receiving a fixation element to be used for the repair of peri-implant fractures without the need for a separate fixation element.

SUMMARY OF THE TECHNOLOGY

In accordance with an aspect of the technology, a fixation system may include an elongate plate which may include an inner wall. The inner wall may have a longitudinal axis. The fixation system may include an extension plate that may have first and second attachment portions that may be offset from one another. An engagement portion may extend outwardly from the first attachment portion. The engagement portion may be couplable to the inner wall of the elongate plate. The second attachment portion may define an aperture through which a fastener may be received. The second attachment portion of the extension plate may be revolvable about the longitudinal axis of the inner wall when the engagement portion of the first attachment portion of the extension plate is coupled to and movable about the inner wall.

In some arrangements, the inner wall of the elongate plate may define an aperture that may extend through a thickness of the elongate plate.

In some arrangements, the first and second attachment portions of the extension plate may be fixed relative to each other. In this manner, when the first attachment portion is movable about the inner wall of the elongate plate, the second portion may be revolvable about an arc.

In some arrangements, the fixation system may include a fastener that may be received at least partially within the engagement portion of the first attachment portion of the extension plate. The fastener may prevent movement of the first attachment portion of the extension plate about the longitudinal axis of the inner wall of the elongate plate. Prior to insertion of the fastener, the first attachment portion of the extension plate may be freely rotatable. In some such arrangements, the longitudinal axis of the inner wall of the elongate plate may be collinear with a longitudinal axis of an aperture defined by the first attachment portion of the extension plate while in other arrangements, the longitudinal axes of the inner wall and the aperture defined by the first attachment portion may be offset from each other. In this manner, the compression acting on the fastener may be greatest within a plane defined by longitudinal axes of the inner wall and the aperture defined by the first attachment portion.

In some arrangements, the fixation system may include a first fastener that may be received within the aperture of the second attachment portion of the extension plate.

In some arrangements, a second fastener may be received at least partially within the engagement portion of the first attachment portion of the extension plate.

In some arrangements, the aperture of the second attachment portion of the extension plate may have a longitudinal axis. In some such arrangements, the longitudinal axis of the inner wall of the elongate plate and the longitudinal axis of the aperture of the second attachment portion of the extension plate may lie along the same plane, in some such arrangements, may form an acute angle with each other.

In some arrangements, the aperture of the second attachment portion of the extension plate may have a longitudinal axis. In some such arrangements, the longitudinal axis of the inner wall of the elongate plate and the longitudinal axis of the aperture of the second attachment portion of the extension plate may be skew relative to each other.

In some arrangements, the elongate plate may include a side surface. In some such arrangements, revolution of the second attachment portion of the extension plate about the longitudinal axis of the inner wall may be bounded by the side surface.

In some arrangements, the elongate plate may include top and bottom surfaces and may have a thickness between such top and bottom surfaces. In some such arrangements, the second attachment portion of the extension plate may extend at least partially below the top surface of the elongate plate. In some such arrangements, the second attachment portion of the extension plate may extend at least partially below the bottom surface of the elongate plate.

In some arrangements, the elongate plate may include a second inner wall that may have a longitudinal axis. In some such arrangements, the fixation system may include a second extension plate. The second extension plate may have first and second attachment portions. An engagement portion of the first attachment portion may be coupled to the second inner wall of the elongate plate. The second attachment portion may have an aperture through which a fastener may be received. In some such arrangements, the second attachment portion of the second extension plate may be revolvable about the longitudinal axis of the second inner wall when the engagement portion of the first attachment portion of the second extension plate is coupled to and movable about the second inner wall.

In some arrangements of the fixation system having a second extension plate, the inner wall and the second inner wall of the elongate plate may be directly adjacent to each other. In some such arrangements, the extension plate and the second extension plate may both be movable relative to the elongate plate such that a longitudinal axis of the aperture of the second attachment portion of the extension plate is movable to lie along the same plane as a longitudinal axis of the second aperture of the second attachment portion of the second extension plate.

In some arrangements, the fixation system may include a first fastener that may be received within the aperture of the second attachment portion of the extension plate. In some arrangements, a second fastener may be received within the aperture of the second attachment portion of the second extension plate. In this manner, the extension plate and the second extension plate may be rotated such that longitudinal axes defined by the first and second fasteners received within the apertures of the respective second attachment portions lie along parallel planes.

In some arrangements, the aperture of the second attachment portion of the extension plate and the aperture of the second attachment portion of the second extension plate may each have a longitudinal axis. The longitudinal axis of the aperture of the second attachment portion of the extension plate may intersect with the longitudinal axis of the inner wall of the elongate plate to define a first acute angle. The longitudinal axis of the aperture of the second attachment portion of the extension plate may intersect with the longitudinal axis of the second inner wall of the plate to define a second acute angle. In some such arrangements, the first and the second acute angles may be different.

In accordance with an aspect of the technology, an extension plate for at least partial receipt within an elongate plate may have at least one inner wall that may define an aperture. Such an extension plate may include a body. The extension plate may further include a plug segment and may include a receiving segment. The plug segment may extend from the body for receipt within the extension plate. The plug segment may have a surface that may be compressible against and that may be rotatable within the inner wall of the aperture of the elongate plate. The receiving segment may have at least one inner surface that may define an aperture for receiving a fastener. Such an inner surface may have a longitudinal axis. Upon rotation of the plug segment, the longitudinal axis of the inner surface of the receiving segment may move along an arc.

In some arrangements, the plug segment may include a plurality of circumferentially spaced apart teeth. These teeth may contact the inner wall of the elongate plate during compression of the plug segment against the inner wall of the elongate plate.

In some arrangements, the inner wall of the elongate plate may be threaded. In some such arrangements, the plug segment may include at least one lip for engagement with the threaded inner wall of the elongate plate.

In some arrangements, the plug segment may include three circumferentially spaced-apart legs. Such legs may be deflectable. In some such arrangements, the legs may be compressible against the inner wall of the elongate plate.

In some arrangements, a lip may protrude from a bottom edge of at least one of the spaced-apart legs of the plug segment.

In some arrangements, one end of circumferentially spaced-apart ends of any lip protruding from the plug segment may be rounded.

In some arrangements, the surface of the plug segment may include an upper portion and a lower portion extending from the upper portion. The upper portion of the plug segment may define a larger perimeter than the lower portion of the plug segment. The upper and lower portions of the plug segment may be compressible against corresponding upper and lower portions of the inner wall of the elongate plate. In some arrangements, the upper portion of the inner wall of the elongate plate may define a larger perimeter than the lower portion of the inner wall of the elongate plate.

In some arrangements, the plug segment may be adapted to receive a fastener. In some arrangements, each of the upper and lower portions of the plug segment may be generally cylindrical in shape and may define respective apertures each having a longitudinal axis. In some such arrangements, the longitudinal axes of the upper and lower portions of the plug segment may be collinear. In other such arrangements, the longitudinal axis of the upper portion may be parallel to and offset from the longitudinal axis of the lower portion. In this manner, when the plug segment is received within the inner wall of the elongate plate and a fastener is received in the plug segment, the compression acting on the fastener may be greatest within a plane defined by the parallel and offset longitudinal axes of the upper and lower portions of the plug segment.

In some arrangements, the inner wall of the plug segment may define a longitudinal axis. In some such arrangements, the longitudinal axes of the inner wall of the plug segment and the inner surface of the receiving segment may be nonparallel.

In some arrangements, the thicknesses of both the plug segment and the receiving segment may be greater than the thickness of the body.

In accordance with an aspect of the technology, an osteosynthesis of a bone part or fragment may be performed. In such an aspect, a first fastener may be received into a first portion of an extension plate to attach the extension plate to an elongate plate. In such an aspect, a second fastener may be received into a second portion of the extension plate and into a bone part or fragment. In this manner, the first portion of the extension plate may be rotatable such that the second portion of the extension plate may be moveable relative to the elongate plate. In some arrangements, the second portion of the extension plate may be revolvable about a longitudinal axis of the first portion of the extension plate.

In some arrangements, the second fastener, when received in the second portion of the extension plate, may be positioned such that the second fastener does not contact an intramedullary implant in the respective bone part or fragment upon its insertion into the respective bone part or fragment.

In some arrangements, the first and second portions of the extension plate may be fixed relative to each other such that when the first portion is rotated, the second portion is movable about an arc.

In some arrangements, a third fastener may be inserted into a first portion of a second extension plate to attach the second extension plate to the elongate plate. In some such arrangements, a fourth fastener may be inserted into a second portion of the second extension plate and into the respective bone part or another bone part. In this manner, the first portion of the second extension plate may be rotatable such that the second portion of the second extension may be movable relative to the elongate plate. In some arrangements, the second portion of the second extension plate may be revolvable about a longitudinal axis of the first portion of the second extension plate.

DETAILED DESCRIPTION OF THE TECHNOLOGY

Figure 1:
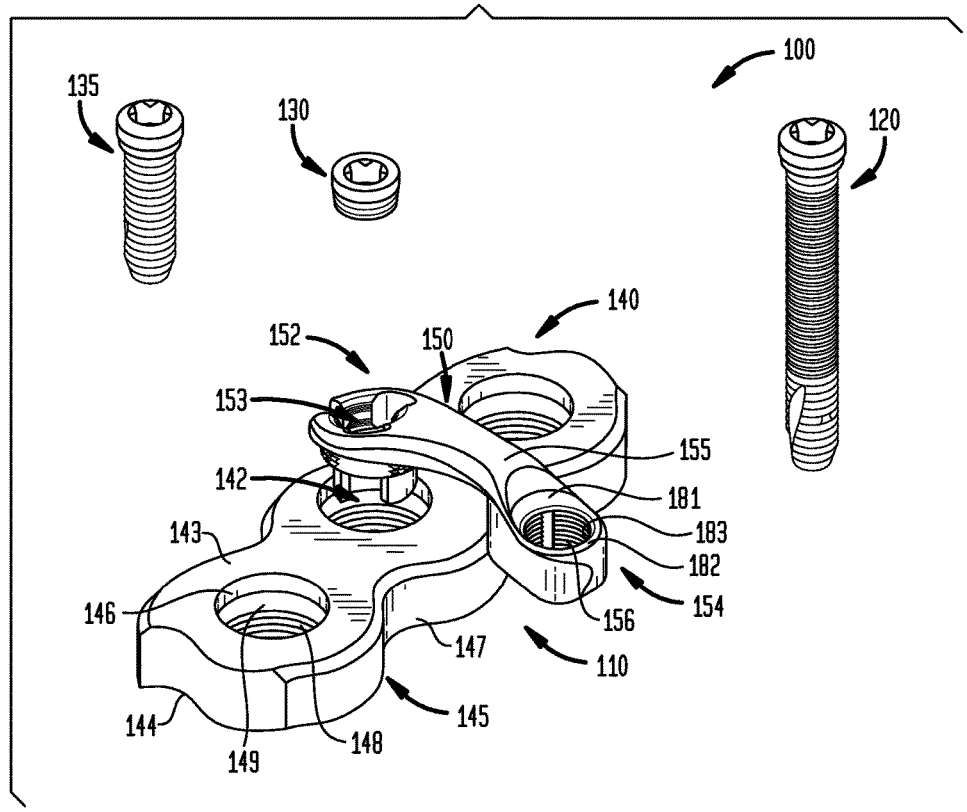
FIG. 1 is an exploded perspective cutaway view of a fixation system, including a plate, an extension plate and optional blind or fixation fasteners, in accordance with an embodiment.

Referring now to the drawings, as shown in FIG. 1, fixation system 100 may include a fixation device 110 and a set of fasteners 120, 130, 135. Fixation device 110 may include a main plate 140, which may be but is not limited to being elongated, and an extension plate 150. Main plate 140 may include a plurality of inner walls 142 separated from each other and extending through a thickness of main plate 140 to define apertures through plate 140. As shown, each inner wall 142 may include an upper section 146 and a lower section 148. Upper section 146 may have a larger circumference than lower section 148 of inner wall 142. As in this example, upper section 146 may be unthreaded and lower section 148 may be threaded. Inner wall 142 may include a step 149 at a transition between upper section 146 and lower section 148, in which step 149 may be a chamfer between upper and lower sections 146, 148.

Main plate 140 may include top and bottom surfaces 143, 144 that may be spaced apart to define the thickness of main plate 140. Side surfaces 145 may extend between top and bottom surfaces 143, 144 and may define one or more grooves or concave contours 147. Main plate 140 may be but is not limited to being made of titanium and its alloys, steel and its alloys including high strength steel, silver, and gold.

Figure 2:
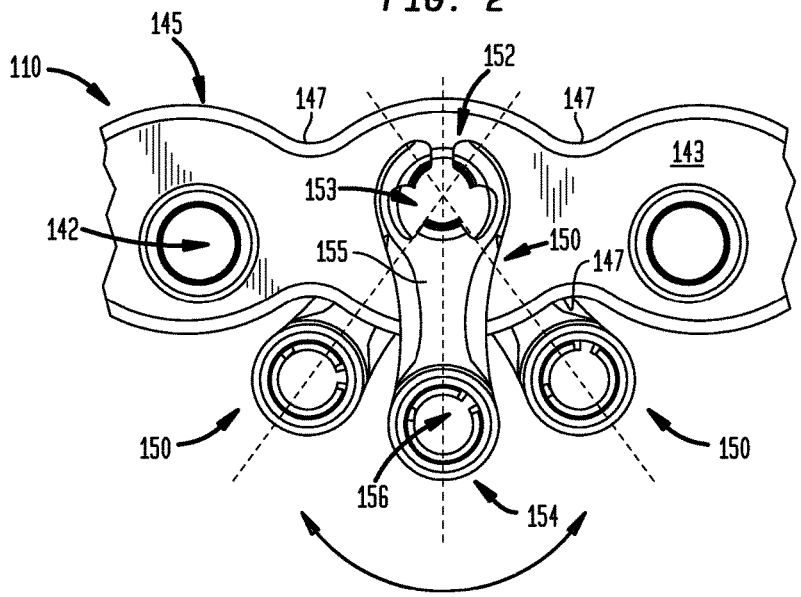
FIG. 2 is an assembled plan cutaway view of the plate and extension plate of FIG. 1, the extension plate being shown in full in one possible location and shown partially in two other possible locations.

As shown in FIGS. 1 and 2, a first attachment portion 152, which may be but is not limited to being a plug segment, of extension plate 150 may be inserted within and attached to inner wall 142 of main plate 140. Extension plate 150 may include a second attachment portion 154 which may be attached to and thereby spaced a fixed distance from first attachment portion 152 by body 155 of extension plate 150. Body 155 may have a narrow profile relative to the first and second attachment portions 152, 154. First attachment portion 152 may be rotatable about a longitudinal axis of inner wall 142 passing through main plate 140 such that second attachment portion 154, which may be but is not limited to being a receiving segment, may be revolvable about the longitudinal axis of inner wall 142. Extension plate 150 may be but is not limited to being made of titanium and its alloys, steel and its alloys including high strength steel, silver, and gold.

Figure 3:
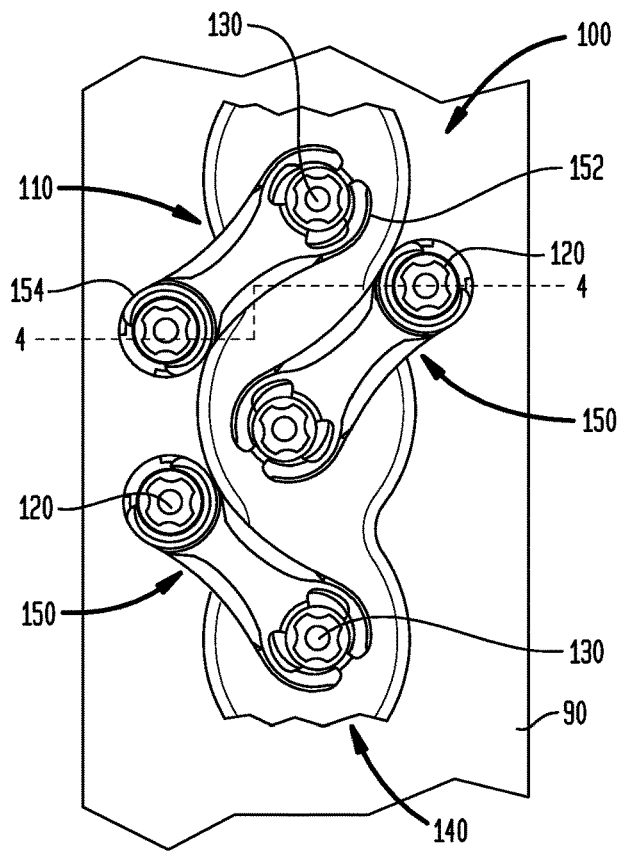
FIG. 3 is a plan view of a fixation system including the fixation system of FIG. 1, in which two additional extension plates are attached to the plate as well as to a bone by fasteners.
Figure 4:
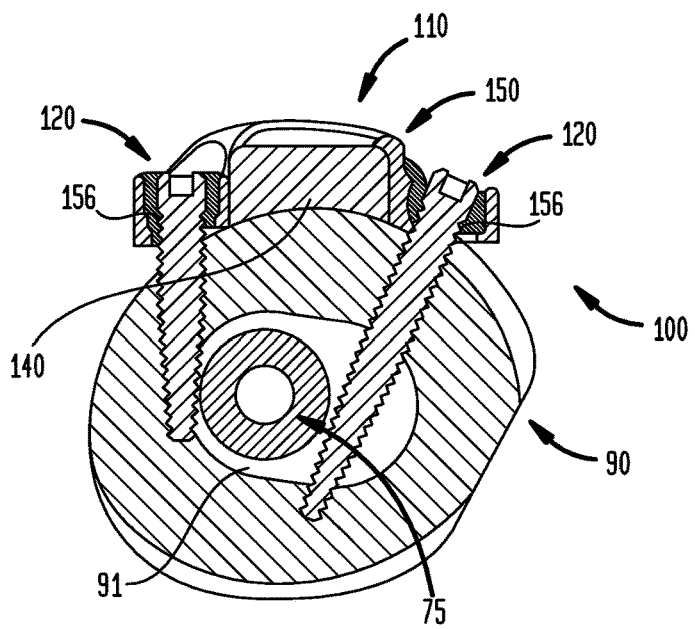
FIG. 4 is a cross-sectional view of the fixation system of FIG. 3 along lines 4-4.

As illustrated in FIGS. 3 and 4 and described further herein, fastener 120 may be inserted into second attachment portion 154 for attachment with another object, such as bone. In preferred arrangements, fastener 120 may be locking screws, although fastener 120 may also be compression screws or other types of fasteners. When first attachment portion 152 is inserted within and attached to inner wall 142 of main plate 140, rotation of first attachment portion 152 may allow relative adjustment of second attachment portion 154 to a predetermined position along an arc. In this manner, fixation device 110 may be placed into various configurations such that fastener 130 may be placed in different predetermined positions based on the needs of a user of the fixation system 100.

First attachment portion 152 of extension plate 150 may be attached to main plate 140 by insertion of one of optional fasteners 130 or 135 into an inner part 153 defining an aperture of first attachment portion 152. In the example of FIG. 1, fastener 130 is a blind locking screw and fastener 135 is a locking screw longer than the blind locking screw that, when inserted into fixation device 110, may extend beyond bottom surface 144 of main plate 140. Insertion of either of fastener 130 and fastener 135 into inner part 153 may expand first attachment portion 152 such that first attachment portion 152 compresses into inner wall 142 of main plate 140. In this manner, first attachment portion 152 may be fixed in position in inner wall 142 and may not be rotatable.

As best illustrated in FIG. 2, second attachment portion 154 of extension plate 150 may be revolved such that extension plate 150 contacts a side surface 145 of main plate 150. As shown in this example, second attachment portion 154 may contact one location along side surface 145 when second attachment portion 154 is revolved in a first direction and may contact another location along side surface 145 when second attachment portion 154 is revolved in a second direction opposite the first direction. In this manner, an arc of revolution of extension plate 150 may be bound by side surface 145.

As further illustrated in the example of FIG. 2, second attachment portion 154 of extension plate 150 may have a convex contour such that a part of second attachment portion 154 fits within one or more of grooves 147 of side surface 145 of main plate 140. A pair of grooves 147 along side surface 145 of main plate 140 may be spaced apart such that part of second attachment portion 154 of extension plate 150 may fit within one of the pair of grooves 147 when second attachment portion 154 is revolved in a first direction and fit within the other of the pair of grooves 147 when second attachment portion 154 is revolved in a second direction opposite the first direction.

Referring now to FIGS. 3 and 4, fixation device 110 may include a plurality of extension plates 150. Fasteners 120, which may be of various sizes, may be inserted into second attachment portions 154 of the plurality of extension plates 150. In this example, second attachment portions 154 may be adjacent to opposing side surfaces 145 of main plate 140 and may be revolved to a predetermined location about a longitudinal axis of respective inner walls 142 of main plate 140, in the manner described previously herein with respect to FIGS. 1 and 2. Respective second attachment portions 154 of the plurality of extension plates 150 may include inner surfaces 156 defining apertures extending through a thickness of the second attachment portions 154. When inserted into inner surfaces 156, fasteners 120, may extend into bone 90 to attach fixation device 110 to bone 90 and to lock second attachment portions 154 into position. As shown, second attachment portions 154 may be spaced a fixed distance from first attachment portions 152 of respective extension plates 150 such that fasteners 120, when inserted in second attachment portions 154 may not intersect with a central region of bone 90 and moreover, may not intersect with a prosthesis 75 that may be inserted within bone 90. As in the example shown, prosthesis 75 may be an intramedullary nail extending longitudinally through medullary canal 91 in a central region of bone 50.

As shown in FIG. 3, second attachment portion 154 of first extension plate 150 of the plurality of extension plates 150 may be revolved about the longitudinal axis of first inner wall 142 of the plurality of inner walls 142 by rotating first attachment portion 152 of first extension plate 150 in one direction while second attachment portion 154 of second extension plate 150 of the plurality of extension plates 150 may be revolved about the longitudinal axis of second inner wall 142 of the plurality of inner walls 142 by rotating first attachment portion 152 of second extension plate 150 in a second direction opposite the first direction. In this manner, as in the example shown, longitudinal axes of inner surfaces 156 of second attachment portions 154 may lie in parallel planes, and in some instances (not shown), the longitudinal axes of inner surfaces 156 of adjacent second attachment portions 154 may be parallel. Having the longitudinal axes of inner surface 156 of attachment portions 154 and inner walls 142 in the same plane, as in the example shown, through the use of extension plate 150 which may be visible to a surgeon, may provide a visual guideline for the surgeon during insertion of fasteners 120, 130, 135.

Figure 5A:
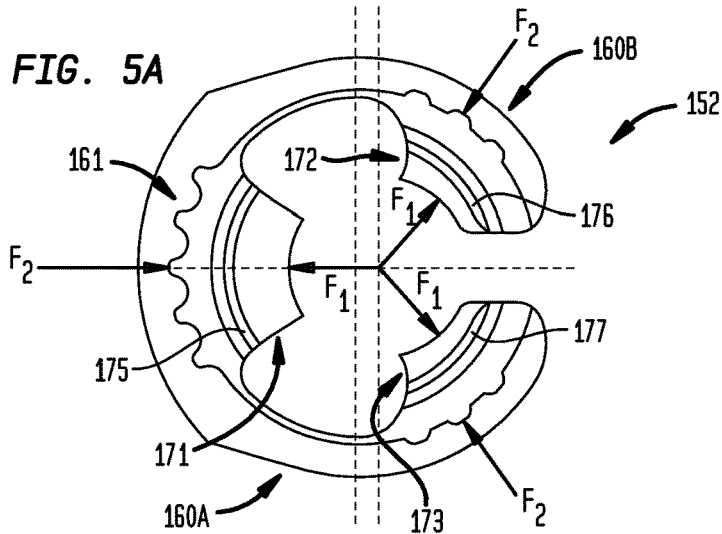
FIGS. 5A-5C are bottom plan, elevation, and top plan views, respectively, of an attachment portion of the extension plate of FIG. 1.
Figure 5B:
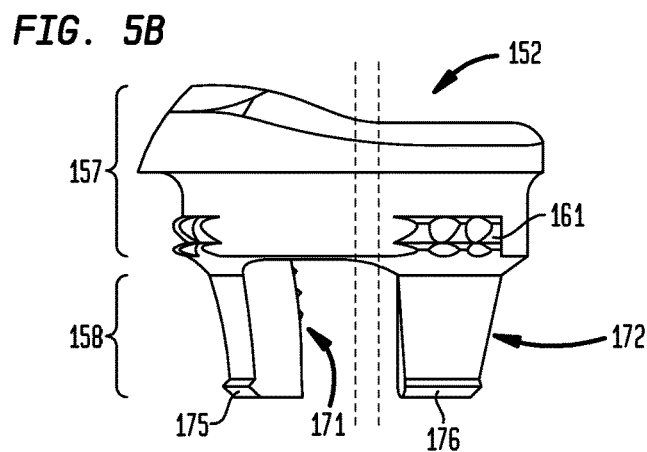
Figure 5C:
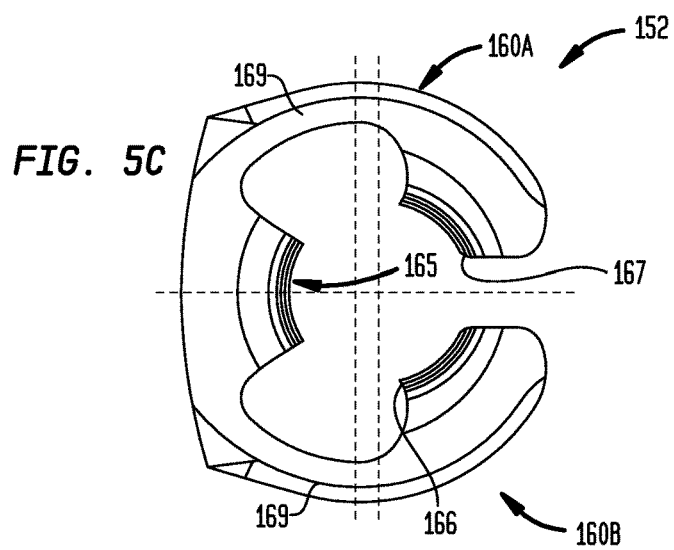

Referring now to FIGS. 5A-5C, first attachment portion 152 includes an upper portion 157, a lower portion 158 extending from the upper portion 157, and an intermediate portion 159 at a transition between upper and lower portions 157, 158. First attachment portion 152 may be in the form of two arms 160A, 160B each including parts of upper portion 157, lower portion 158, and intermediate portion 159 in which a gap is defined between arms 160A, 160B. Arms 160A, 160B may be symmetrical and may be cantilevered within a plane transverse to a longitudinal axis of inner part 153 of first attachment portion 152. At a transition 169 from body 155, each of arms 160A, 160B may have a thin lateral profile to enhance their flexibility and reduce energy losses during deformation of either or both of arms 160A, 160B and internal threads 165 upon insertion of a fastener.

As shown, upper portion 157 may define a larger perimeter along its entire length than lower portion 158. Upper and lower portions 157, 158 of first attachment portion 152 may have generally cylindrical or conical shapes. Upper portion 157 may include a plurality of, and in example shown three, sets of teeth 161 circumferentially spaced about its external circumference. Upper portion 157 may include an internal thread 165, which may be conical, on internal bosses 163 of upper portion 157. In this manner, as shown, internal thread 165 may be split into three parts. As best shown in FIG. 5C, internal thread 165 may include a sharp edge 166 at a beginning of thread 165 and may include a rounded edge 167 at an end of thread 165.

Lower portion 158 may include three circumferentially spaced apart legs 171, 172, 173. Legs 172, 173 may be on arms 160A, 160B, respectively, and may be symmetrical. Leg 171 may be nearest to body 155 of extension plate 150 of the three legs 171-173. Leg 171 may include middle lip 175 protruding outwardly along a bottom edge of leg 171, and legs 172, 173 may include outer lips 176, 177, respectively, protruding outwardly along their bottom edges. At the gap between arms 160A, 160B, outer lips 176, 177 may be rounded.

With reference to FIG. 1 and FIGS. 5A-5C, teeth 161 may define an outer circumference of upper portion 157 of first attachment portion 152 of extension plate 150 that is substantially similar to the circumference of upper section 146 of inner wall 142 of main plate 140. In this manner, when first attachment portion 152 of extension plate 150 is inserted into inner wall 142 of main plate 140, upper portion 157 of first attachment portion 152 may be slightly compressed against upper section 146 of inner wall 142 of main plate 140. Each of legs 171-173 of lower portion 158 of extension plate 150 may be flexible such that legs 171-173 deflect upon their insertion into lower section 148 of inner wall 142 of main plate 140. The respective lips 175-177 of legs 171-173 may be dimensioned to have a thickness such that upon insertion of legs 171-173 into lower section 148 of inner wall 142 of main plate 140, lips 175-177 may extend into the threads of lower section 148 of inner wall 142. In this manner, first attachment portion 152 of extension plate 150 may be held within inner wall 142 of main plate 140 with sufficient force such that extension plate 150 may be manipulated by a user, including by rotation about the longitudinal axis of inner wall 142, without backing out of inner wall 142.

As further shown in each of FIGS. 5A-5C, a longitudinal axis of upper portion 157 may be parallel to and offset from a longitudinal axis of lower portion 158 of first attachment portion 152 within a plane passing through first and second attachment portions 152, 154 of extension plate 150. In this manner, when a fastener, such as fasteners 130 or 135, is inserted into first attachment portion 152, the forces acting on upper portion 157 may be greater than forces acting on lower portion 158 of first attachment portion 152.

Figure 6A:
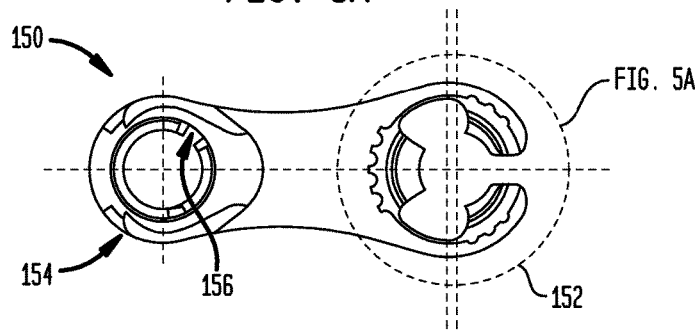
FIGS. 6A-6C are bottom plan, elevation, and top plan cutaway views, respectively, of the extension plate of FIG. 1.
Figure 6B:
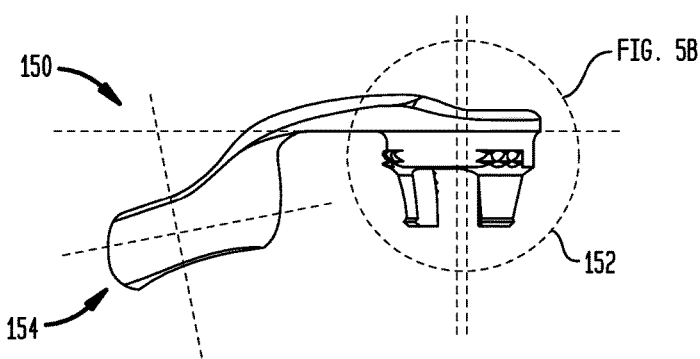
Figure 6C:
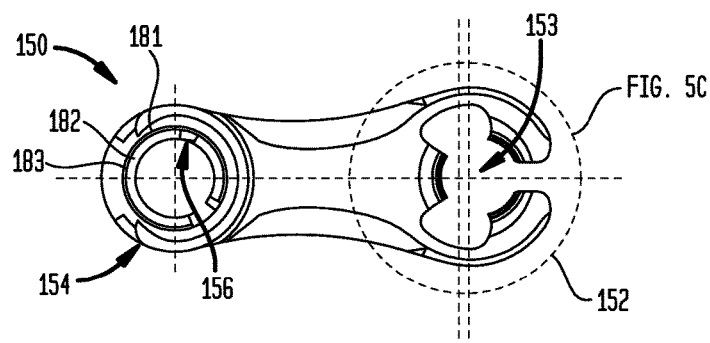

Referring now to FIGS. 6A-6C, second attachment portion 154 of extension plate 150 may include upper part 181 that may be unthreaded, lower part 182 that may be threaded, and middle part 183 that may be chamfered. In this manner, second attachment portion 154 may receive a fastener, such as fastener 120, which may be a locking screw as described previously herein. As illustrated by the combination of FIGS. 6A-6C, the longitudinal axis of inner surface 156 of second attachment portion 154 may be in the same plane as the longitudinal axis of inner part 153 of first attachment portion 152. As further illustrated, the longitudinal axes of inner surface 156 and inner part 153 may intersect.

Referring again to the example of FIG. 1, in operation, such as one which may be conducted by a surgeon during a medical osteosynthesis procedure to treat a periprosthetic fracture, main plate 140 may be fastened to a bone by fasteners, which may be but are not limited to being locking screws as shown, compression screws, or other appropriate fixation members. Prior to or subsequent to the fastening of main plate 140 to the bone, first attachment portion 152 of extension plate 150 may be pressed, such as by snapping, into an aperture defined by one of the plurality of inner walls 142 of main plate 140. First attachment portion 152 may be rotated about the longitudinal axis of inner wall 142 of main plate 140 such that second attachment portion 154 is revolved along an arc about the longitudinal axis of inner wall 142. Fastener 130 or 135 then may be inserted, and as shown threaded, into inner part 153 of first attachment portion 152 to lock relative rotation and translation between extension plate 150 and main plate 140. Fastener 120 then may be inserted, and as shown threaded, into inner surface 156 of second attachment portion 154 to attach second attachment portion 154 to another object, such as bone as shown in FIGS. 3 and 4. The order of insertion of fastener 130 and fastener 120 may be reversed in some arrangements.

In some arrangements in accordance with the present technology, the main plate may be a bone plate for attachment to either of or both a diaphysis and epiphysis of a trabecular bone, such as a femur, tibia, humerus, or radius. The inner walls of the main plate may be placed in various locations and may include at least one series of three or more inner walls that may or may not be aligned along an axis through centers of the inner walls.

In some arrangements in accordance with the present technology, fasteners 130, 135 may be rivets which may be used to attach the first attachment portion of the extension plate to the main plate.

In some alternative arrangements of a fixation device in accordance with the present technology, an extension plate, such as extension plate 150, may include a plurality of additional attachment portions extending from a first attachment portion of the extension plate. In such arrangements, each of the additional attachment portions may have an inner surface for receiving a fastener that may attach the respective additional attachment portions to another object or objects, such as but not limited to one or more bones.

In some arrangements of a fixation device in accordance with the present technology, the fixation device may include a second extension plate that may be attached to a first extension plate, extending from a main plate, such as main plate 140. In some such arrangements, the first extension plate may include a first attachment portion similar to the first attachment portion of extension plate 150, as described previously herein, and a second attachment portion that may include an inner surface similar to the inner walls of main plate 140, as described previously herein. In some such arrangements, second extension plate may have first and second attachment portions similar to extension plate 150, as described previously herein. In this manner, the first attachment portion of the second extension plate may be rotatable about a longitudinal axis of the inner surface of the second attachment portion of the first extension plate such that the second attachment portion of the second extension plate may be revolvable about the longitudinal axis of the inner surface of the second attachment portion of the first extension plate.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the technology, and in the technology generally.

Furthermore, although the technology disclosed herein has been described with reference to particular features, it is to be understood that these features are merely illustrative of the principles and applications of the present technology. It is therefore to be understood that numerous modifications, including changes in the sizes of the various features described herein, may be made to the illustrative embodiments and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the claims set forth below.

The invention claimed is:

1. A fixation system comprising:
an elongate plate including an inner wall defining a longitudinal axis thereof; and
an extension plate having first and second attachment portions offset from one another, the first attachment portion including a base for receipt in the elongate plate and a projection coupleable to the inner wall of the elongate plate and extending outwardly from the base in a direction transverse to the longitudinal axis of the elongate plate when the projection is coupled to the inner wall of the elongate plate, and the second attachment portion defining a longitudinal axis thereof and including an aperture for receiving a fastener therethrough,
wherein the second attachment portion of the extension plate is revolvable about the longitudinal axis of the inner wall when the first attachment portion of the extension plate is coupled to and movable about the inner wall, and
wherein the longitudinal axes defined by the inner wall of the elongate plate and the aperture of the second attachment portion of the extension plate are nonparallel when the extension plate is detached from the elongate plate.

2. The fixation system of claim 1, wherein the inner wall of the elongate plate defines an aperture extending through a thickness of the elongate plate.

3. The fixation system of claim 1, wherein the first and second attachment portions of the extension plate are fixed relative to each other such that when the first attachment portion is movable about the inner wall of the elongate plate, the second portion is revolvable about an arc.

4. The fixation system of claim 1, further comprising a fastener received at least partially within the first attachment portion of the extension plate to prevent movement of the first attachment portion of the extension plate about the longitudinal axis defined by the inner wall of the elongate plate, wherein prior to insertion of the fastener, the first attachment portion of the extension plate is freely rotatable within the inner wall of the elongate plate.

5. The fixation system of claim 1, further comprising:
a first fastener received within the aperture of the second attachment portion of the extension plate.

6. The fixation system of claim 5, further comprising:
a second fastener received at least partially within the first attachment portion of the extension plate.

7. The fixation system of claim 1, wherein the longitudinal axis defined by the inner wall of the elongate plate and the longitudinal axis defined by the aperture of the second attachment portion of the extension plate lie along the same plane and form an acute angle with each other.

8. The fixation system of claim 1, wherein the longitudinal axis defined by the inner wall of the elongate plate and the longitudinal axis defined by the aperture of the second attachment portion of the extension plate are skew relative to each other.

9. The fixation system of claim 1, wherein the elongate plate includes a side surface and revolution of the second attachment portion of the extension plate about the longitudinal axis defined by the inner wall of the elongate plate is bounded by the side surface.

10. The fixation system of claim 1, wherein the elongate plate includes top and bottom surfaces and a thickness therebetween, and wherein the second attachment portion of the extension plate extends at least partially below the top surface of the elongate plate when the first attachment portion of the extension plate is coupled to and movable about the inner wall.

11. The fixation system of claim 1, wherein the elongate plate includes a second inner wall defining a longitudinal axis thereof, the fixation system further comprising:
a second extension plate having first and second attachment portions, an engagement portion of the first attachment portion of the second extension plate coupled to the second inner wall of the elongate plate and the second attachment portion of the second extension plate having an aperture for receiving a fastener therethrough, wherein the second attachment portion of the second extension plate is revolvable about the longitudinal axis of the second inner wall when the engagement portion of the first attachment portion of the second extension plate is coupled to and movable about the second inner wall.

12. The fixation system of claim 11, wherein the inner wall and the second inner wall of the elongate plate are directly adjacent to each other, and wherein the extension plate and the second extension plate are both movable relative to the elongate plate such that the longitudinal axis defined by the aperture of the second attachment portion of the extension plate can be moved to lie along the same plane as a longitudinal axis defined by the second aperture of the second attachment portion of the second extension plate.

13. The fixation system of claim 12, further comprising:
a first fastener received within the aperture of the second attachment portion of the extension plate; and
a second fastener received within the aperture of the second attachment portion of the second extension plate,
wherein the extension plate and the second extension plate can be rotated such that longitudinal axes defined by the first and second fasteners received within the apertures of the respective second attachment portions lie along parallel planes.

14. The fixation system of claim 11, wherein the aperture of the second attachment portion of the second extension plate each define a longitudinal axis, wherein the longitudinal axis defined by the aperture of the second attachment portion of the extension plate intersects with the longitudinal axis defined by the inner wall of the elongate plate to define a first acute angle, wherein the longitudinal axis defined by the aperture of the second attachment portion of the second extension plate intersects with the longitudinal axis defined by the second inner wall of the elongate plate to define a second acute angle, and wherein the first and the second acute angles are different.

15. An extension plate for at least partial receipt within an elongate plate having at least one inner wall defining an aperture, comprising:
a body;
a plug segment extending from the body for receipt within the elongate plate, the plug segment having a plug segment surface compressible against and rotatable within the inner wall of the aperture of the elongate plate and having an aperture opposite the plug segment surface defining a longitudinal axis thereof; and
a receiving segment having at least one inner surface defining an aperture for receiving a fastener, the inner surface defining a longitudinal axis thereof,
wherein the longitudinal axes defined by the aperture of the plug segment and inner surface of the receiving segment are nonparallel, and
wherein upon rotation of the plug segment, the longitudinal axis defined by the inner surface of the receiving segment moves along an arc.

16. The extension plate of claim 15, wherein the plug segment includes a plurality of circumferentially spaced apart teeth for contacting the inner wall of the elongate plate during compression of the plug segment against the inner wall of the elongate plate.

17. The extension plate of claim 15, wherein the inner wall of the elongate plate is threaded, and wherein the plug segment includes at least one lip for engagement with the threaded inner wall of the elongate plate.

18. The extension plate of claim 15, wherein the plug segment includes three circumferentially spaced-apart and deflectable legs, the legs being compressible against the inner wall of the elongate plate.

19. The extension plate of claim 18, wherein a lip protrudes from a bottom edge of at least one of the spaced-apart legs of the plug segment.

20. The extension plate of claim 19, wherein one end of the lip protruding from the plug segment is rounded.

21. The extension plate of claim 15, wherein the surface of the plug segment includes an upper portion and a lower portion extending therefrom, the upper portion defining a larger perimeter than the lower portion of the plug segment, the upper and lower portions of the plug segment being compressible against corresponding upper and lower portions of the inner wall of the elongate plate, the upper portion of the inner wall of the elongate plate defining a larger perimeter than the lower portion of the inner wall of the elongate plate.

22. The extension plate of claim 21, the plug segment adapted to receive a fastener therein, wherein each of the upper and lower portions of the plug segment are generally cylindrical in shape and have apertures each defining a longitudinal axis thereof, and wherein the longitudinal axis defined by the upper portion is parallel to and offset from the longitudinal axis defined by the lower portion such that when the plug segment is received within the inner wall of the elongate plate and a fastener is received in the plug segment, the compression acting on the fastener may be greatest within a plane defined by the longitudinal axes defined by the upper and lower portions of the plug segment.

23. The extension plate of claim 15, wherein the inner wall of the plug segment defines a longitudinal axis thereof, and wherein the longitudinal axes of the apertures defined by the plug segment and inner surface of the receiving segment lie along the same plane and form an acute angle with each other.

24. The extension plate of claim 15, wherein the thicknesses of both the plug segment and the receiving segment are greater than the thickness of the body.

25. A method of performing osteosynthesis of a bone part or fragment, comprising:
   receiving a first fastener into a first portion of an extension plate defining a longitudinal axis, wherein the first portion of the extension plate extends into a hole defined by an inner wall of an elongate plate to attach the extension plate to the elongate plate such that the first fastener does not contact the elongate plate and such that the first portion of the extension plate lies between the first fastener and the inner wall; and
   receiving a second fastener into a second portion of the extension plate and into a bone part or fragment, the second portion of the extension plate defining a longitudinal axis, wherein the longitudinal axes defined by the first and second portions of the extension plate are nonparallel when the extension plate is detached from the elongate plate, and wherein the first portion of the extension plate is rotatable such that the second portion is movable relative to the elongate plate.

26. The method of claim 25, wherein the second fastener does not contact an intramedullary implant received in the respective bone part or fragment upon insertion of the second fastener into the respective bone part or fragment.

27. The method of claim 25, wherein the first and second portions of the extension plate are fixed relative to each other such that when the first portion is rotated, the second portion is movable about an arc.

28. The method of claim 25, further comprising:
   inserting a third fastener into a first portion of a second extension plate to attach the second extension plate to the elongate plate; and
   inserting a fourth fastener into a second portion of the second extension plate and into the respective bone part or another bone part, wherein the first portion of the second extension plate is rotatable such that the second portion of the second extension plate is movable relative to the elongate plate.

* * * * *